United States Patent [19]
Sperinde et al.

[11] 4,453,218
[45] Jun. 5, 1984

[54] SIGNAL FILTER METHOD AND APPARATUS

[75] Inventors: Johnie M. Sperinde, San Jose; Stanley D. Goldring, Cupertino; Dean T. Miller, Portola Valley, all of Calif.

[73] Assignee: Oximetrix, Inc., Mountain View, Calif.

[21] Appl. No.: 210,032

[22] Filed: Nov. 24, 1980

[51] Int. Cl.³ .......................... H03K 5/20; A61B 5/04
[52] U.S. Cl. .................................. 364/416; 364/572; 128/696; 328/149
[58] Field of Search ............... 364/416, 417, 572, 574, 364/724; 356/41; 128/634, 696; 328/149, 167; 307/356, 360, 543, 556

[56] References Cited

U.S. PATENT DOCUMENTS

| | | | |
|---|---|---|---|
| 3,344,284 | 9/1967 | Thompson | 307/542 |
| 3,848,586 | 11/1974 | Suzuki et al. | 364/417 X |
| 3,894,222 | 7/1975 | Siems | 364/574 |
| 3,955,101 | 5/1976 | Amelio et al. | 307/356 |
| 3,999,084 | 12/1976 | Beaudette | 307/360 X |
| 4,021,653 | 5/1977 | Sharp et al. | 364/724 |
| 4,035,734 | 7/1977 | Flormann et al. | 307/360 X |
| 4,109,643 | 8/1978 | Bond et al. | 356/41 X |
| 4,114,604 | 9/1978 | Shaw et al. | 356/41 X |
| 4,151,471 | 4/1979 | Packard et al. | 455/224 |
| 4,161,945 | 7/1979 | Grossman | 128/696 |
| 4,167,331 | 9/1979 | Nielsen | 356/41 X |
| 4,175,256 | 11/1979 | Dolikian | 328/149 |
| 4,266,554 | 5/1981 | Hamaguri | 364/416 X |

Primary Examiner—Edward J. Wise
Attorney, Agent, or Firm—Lyon & Lyon

[57] ABSTRACT

A signal filter method and apparatus for removing portions of a signal indicative of erroneous data, an exemplary apparatus including means for receiving the signal, means for adjusting a threshold by increasing the threshold a first predetermined amount when the signal is in a predetermined relationship with the threshold and for decreasing the threshold a second predetermined amount when the signal is in a second predetermined relationship with the threshold, and means for comparing the signal with the adjusted threshold and for transmitting the signal if the signal bears a first predetermined relationship to the threshold. Disclosed herein are digital and analog implementations of the signal filter method and apparatus, particularly suited for use with catheter-type oximeter apparatus.

40 Claims, 5 Drawing Figures

SIGNAL FILTER METHOD AND APPARATUS

BACKGROUND

The present invention relates generally to signal processing and more particularly to a signal filter method and apparatus suitable for use with in vivo catheter-type oximeters.

Various catheter-type oximeter apparatus are known for determining blood oxygen saturation. One such apparatus is disclosed in U.S. Pat. No. 4,114,604 to Shaw, et al., the disclosure of which is incorporated herein by reference. Typically with such apparatus, a catheter is introduced into a blood vessel and the blood within the vessel flows about the catheter tip. The catheter includes a first fiberoptic guide which conducts radiation from the oximeter apparatus to an aperture at the catheter tip. The blood flowing about the catheter tip scatters a portion of the incident radiation thereon back to a second aperture at the catheter tip where a second fiberoptic guide transmits this back-scattered radiation to the oximeter apparatus. The back-scattered radiation is then analyzed by the oximeter apparatus to provide a measurement of oxygen saturation.

As the blood under test flows about the catheter tip, the amount of radiation returning therefrom exhibits pulsatile fluctuations synchronized with the heartbeat. It is believed that these fluctuations result from the catheter tip impacting or very closely approaching the vessel wall. Since the vessel wall exhibits reflective characteristics not necessarily related to blood oxygen saturation, these substantial fluctuations resulting in greatest part from the reflectance of the vessel wall can introduce inaccuracies into the measurement of blood oxygen.

Various techniques have been utilized in reducing or eliminating these substantial fluctuations. In one system, the time constant or span of the oxygen saturation measurement is increased to thereby decrease the influence that the substantial radiation fluctuations may have on the oxygen saturation calculation. However, this technique does not remove from the oxygen saturation measurement process the erroneous data represented by the substantial radiation fluctuations. Thus, the oxygen saturation calculation is based at least in part upon erroneous data, thereby adversely affecting the accuracy of the oxygen saturation measurement.

In another oximeter apparatus, the catheter tip is enclosed within a cage-type structure in an attempt to prevent the oximeter tip from impacting the vessel wall. While the cage structure may effectively separate the catheter tip from the vessel wall, the structure also greatly increases the tendency for deposits to form on the catheter tip, an undesirable result.

SUMMARY OF THE INVENTION

The method and apparatus of the present invention overcomes the limitations described above and provides a signal filter which removes therefrom portions of the signal indicative of erroneous data. An exemplary signal filter method in accordance herewith may include the steps of receiving the signal, adjusting a threshhold value by increasing the threshhold a first predetermined amount when the signal is in a first predetermined relationship with the threshhold value and decreasing the threshhold a second predetermined amount when the signal is in a second predetermined relationship with the threshhold. The signal is then compared with the adjusted threshhold and transmitted if the signal bears a first predetermined relationship to the threshhold. In one embodiment of the present invention, adjusting the threshhold may include the steps of comparing the signal to a base line, adjusting the base line toward the signal, and then establishing the threshhold as related to the base line. Signal transmission may be inhibited or a predetermined output transmitted in place of the signal.

A signal filter apparatus in accordance with the present invention may include means for receiving the signal, means for adjusting a threshhold by increasing the threshhold a first predetermined amount when the signal is in a first predetermined relationship with the threshhold and for decreasing the threshhold a second predetermined amount when the signal is in a second predetermined relationship with the threshhold, and means for comparing the signal with the adjusted threshhold value and for transmitting the signal if the signal bears a first predetermined relationship to the threshhold. The means for adjusting the threshhold may further include means for comparing the signal to a base line, means for adjusting the base line toward the signal, and means for determining the threshhold related to the base line. The apparatus can also include means for inhibiting the signal or transmitting a predetermined output if the signal bears a second predetermined relationship to the threshhold value.

It is thus seen that an exemplary method and apparatus in accordance herewith removes from the signal those portions of the signal indicative of erroneous data.

Further, in accordance herewith, the signal filter method and apparatus may be incorporated within an oximeter method or apparatus to thereby provide an improved oximeter method and apparatus less susceptible to erroneous reflected radiation received at the catheter tip.

Thus, it is an object of the present invention to provide a signal filter.

It is another object of the present invention to provide an improved oximeter method and apparatus.

It is yet a further object of the present invention to provide an improved oximeter method and apparatus employing a signal filter.

BRIEF DESCRIPTION OF THE DRAWINGS

These and other objects and advantages of the present invention are apparent from a consideration of the entire specification and the following drawings in which:

FIG. 3 is an exemplary flow diagram for implementing a signal filter in accordance with the present invention;

DESCRIPTION

Figure 1:
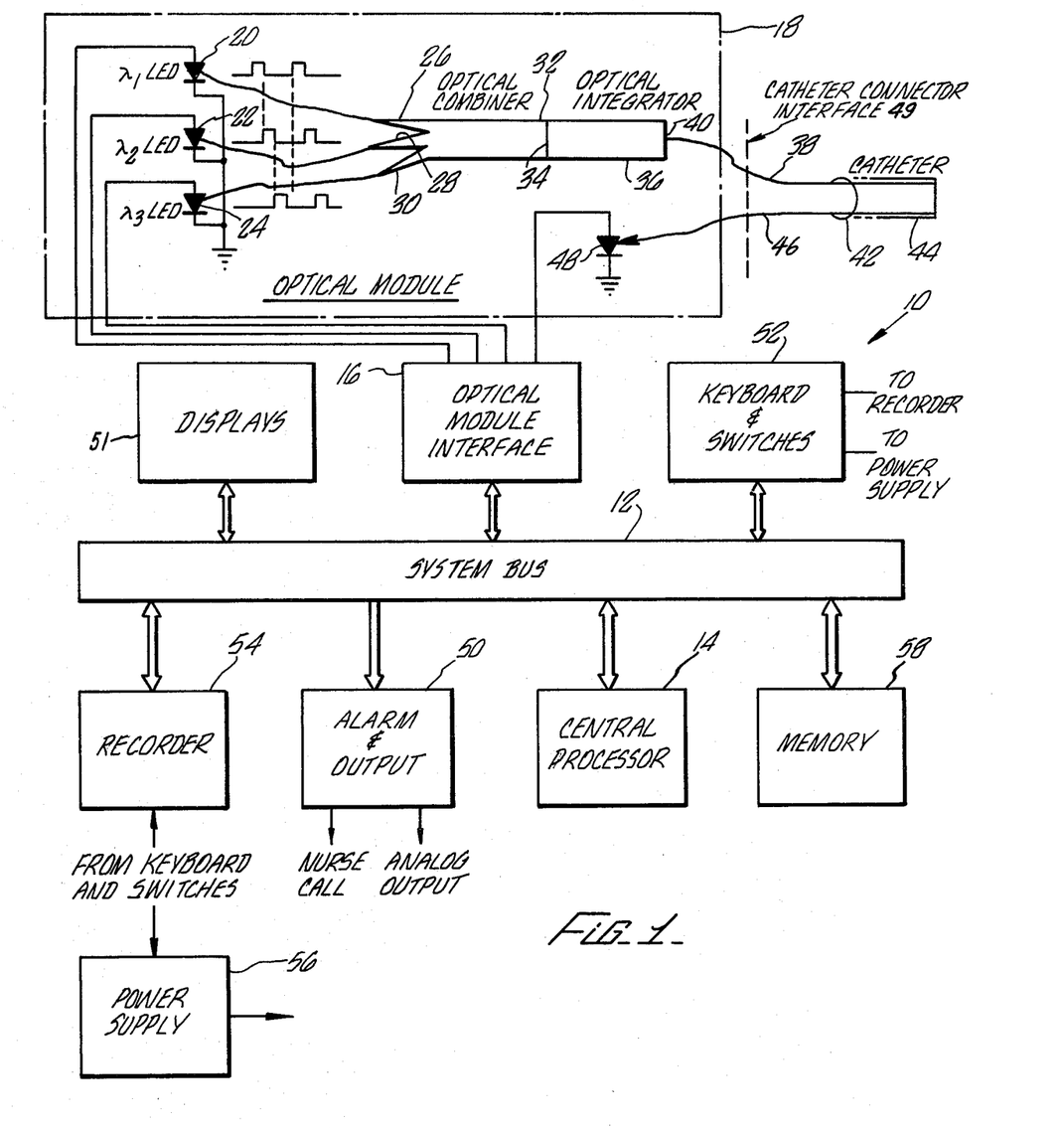
FIG. 1 is a block diagram of an oxygen saturation measurement apparatus suitable for use with the signal filter of the present invention.

With reference now to FIG. 1, an oxygen saturation measuring apparatus 10, sometimes herein referred to as an oximeter or oximeter apparatus, is preferably a microprocessor bus-oriented system, a configuration which is well known to those skilled in the art. More particularly, the apparatus 10 includes a system bus 12 comprising a plurality of conductors for transmitting address, data, program and control information to various portions of the apparatus 10. The apparatus 10 is controlled by a central processor 14, which is connected to and substantially controls the system bus 12. In an exemplary embodiment, the central processor 14 is a type 6800 manufactured by Motorola Semiconductor Products, Inc.

The system bus 12 communicates with an optical module interface 16 which in turn is connected to an optical module 18. The interface 16 drives a plurality of light-emitting diodes (LEDs) 20, 22, and 24, which emit radiation at preselected wavelengths $\lambda_1$, $\lambda_2$ and $\lambda_3$ respectively. This radiation is collected by fiberoptic guides 26, 28, and 30, which conduct the radiation emitted by the diodes 20-24 to an optical combiner 32. The optical combiner 32 in turn transmits radiation through an end cross-section 34 to an optical integrator 36. A transmitting fiberoptic guide 38 is coupled to the exit aperture 40 of the optical integrator 36 and the fiberoptic guide 38 consequently transmits radiation through a catheter 42 to an aperture within a distal tip 44 of the catheter 42. The catheter tip 44 is disposed within a blood vessel and the blood under test flows through the vessel and about the tip 44. As disclosed in the aforementioned U.S. Pat. No. 4,114,604 to Shaw, et al., transmitting fiberoptic guide 38 and second fiberoptic guide 46 of catheter 42 may each consist of only a single optical fiber which greatly simplifies the construction of the catheter and makes possible a low-cost disposable catheter which can be coupled to the optical module 18 at an interface connector 49.

The radiation emitted from the fiberoptic guide 38 is back-scattered by the blood under test and is reflected by the vessel walls. This back-scattered and reflected radiation is then received through a second aperture within the catheter tip 44 by a second fiberoptic guide 46. The fiberoptic guide 46 transmits this radiation to a detector 48 which provides a signal proportional thereto to the optical module interface 16.

With continued reference to FIG. 1, the apparatus 10 further includes various displays 48 responsive to the system bus 12. Furthermore, the system bus 12 is connected to an alarm and output circuit 50 which may provide an audio alert tone for the operator of the apparatus 10, nurse call signals and a suitable auxiliary analog output for driving ancillary equipment. A keyboard and control switches 52 is connected to the system bus 12 and also is directly connected to a recorder 54 and to a power supply 56. The recorder 54 is also responsive to the system bus 12 to produce a permanent strip chart record of the blood oxygen saturation as measured by the apparatus 10. The power supply 56 provides power throughout the apparatus 10.

The central processor 14, through the system bus 12, communicates with a memory 58 which may include program instructions for the central processor 14 in read-only memory (ROM) and which may further include temporary or scratch-pad random-access memory (RAM) for use by the central processor 14 during the operation of the apparatus 10.

In operation, the apparatus 10 is controlled by the keyboard and switches 52 to energize the power supply 56. The optical module interface 16 sequentially energizes the diodes 20-24 to sequentially provide radiation at the three preselected wavelengths $\lambda_1$, $\lambda_2$ and $\lambda_3$ via the catheter 42 to the catheter tip 44. Upon back scattering by the blood under test and transmission via the catheter 42 to the detector 48, the optical module interface 16 converts the analog signal from the detector 48 indicative of radiation intensity into a digital signal which in the embodiment of FIG. 1 may be 12 bits. This digital signal is then applied through the system bus 12 as controlled by the central processor 14 and is stored into the memory 58. The central processor 14 subsequently uses this data stored in the memory 58 to calculate the blood oxygen saturation. For example, the central processor 14 may implement equation 8 from the referenced Shaw, et al., patent, which is as follows:

$$OS = \frac{A_0 + A_1\left(\frac{I_1}{I_2}\right) + A_2\left(\frac{I_1}{I_2}\right)^2 + A_3\left(\frac{I_3}{I_2}\right)}{B_0 + B_1\left(\frac{I_1}{I_2}\right) + B_2\left(\frac{I_1}{I_2}\right)^2 + B_3\left(\frac{I_3}{I_2}\right)}$$

where $A_0$, $A_1$, $A_2$ and $A_3$ are weighting factors or coefficients, $B_0$, $B_1$, $B_2$ and $B_3$ are weighting factors or coefficients, and $I_1$, $I_2$, and $I_3$ are radiation intensities from the blood under test measured at wavelengths $\lambda_1$, $\lambda_2$ and $\lambda_3$, respectively, each normalized with respect to a reference light intensity measurement. Once the calculation is completed, the central processor 14 provides the resulting oxygen saturation (OS) value to the displays 48, and if enabled, to the recorder 54. If the central processor 14 detects that an alarm condition exists, the alarm and output circuit 50 generates an audio alarm tone or a nurse call signal.

It will be understood by those skilled in the art that the apparatus of FIG. 1 is generally a digital implementation of the catheter oximeter apparatus and method which is disclosed in the referenced Shaw, et al., patent. Such a microprocessor-based bus-oriented system will be readily apparent to one skilled in the art. Moreover, other than three radiation intensitites may be used which can provide an oxygen saturation measurement through other suitable mathematical relationships.

Figure 2:
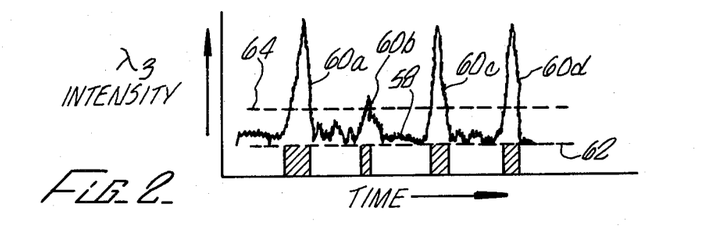
FIG. 2 is an exemplary wave form depicting intensity fluctuations in radiation returning from a catheter tip.

With reference now to FIG. 2, an intensity curve 58 of the back-scattered and reflected radiation from, for example, LED 24 operating at wavelength $\lambda_3$, includes pulsatile fluctuations 60a-60d synchronized with the patient's heartbeat. Although the $\lambda_3$ intensity curve 58 is indicated by a continuous line, it is to be understood that the $\lambda_3$ intensity as detected by the detector 48 in the exemplary embodiment of FIG. 1 is a series of individual intensity measurements which, when plotted together, form the $\lambda_3$ intensity curve 58 of FIG. 2. The pulsatile fluctuations 60a-60d, if of sufficient magnitude, represent erroneous or unsuitable reflected radiation intensities which typically result from the catheter tip 44 impacting or very closely approaching the vessel walls as the catheter tip 44 is moved about within the vessel during a heartbeat. The $\lambda_3$ intensity shown in FIG. 2 is converted by the optical module interface 16 of FIG. 1 into a corresponding digital value which may then be utilized by the central processor 14 as is described below.

Turning now to FIG. 3, a signal filter method flow diagram as shown therein implemented within the apparatus 10 of FIG. 1 advantageously removes from the signals the portions thereof which are indicative or erroneous or unsuitable radiation readings. More particularly, and with continued reference to FIGS. 1 and 3, the central processor 14 reads from the system bus 12 the radiation intensities from the catheter tip at, for example, approximately four millisecond intervals and the control processor 14 sums each of the radiation intensitites individually for a period of time which can be approximately 32 milliseconds. This initially averages the individual radiation intensities and thus slightly smoothes radiation intensities $I_1$, $I_2$ and $I_3$. The central processor 14 then compares the intensity $I_3$ with a base line intensity value which may be temporarily stored within the memory 58.

If the intensity $I_3$ is not greater than the base line intensity value, the central processor 14 decreases the base line value according to the following equation:

$$BL = BL - K_1 \cdot (BL - I_3)$$

where BL is the base line intensity value and $K_1$ is a predetermined constant which can equal approximately 0.25 in an exemplary embodiment.

Once the new base line intensity value is determined, a threshhold intensity value is determined wherein $TH = K_4 \cdot BL$, where TH is the threshhold intensity value and $K_4$ is a predetermined constant which can equal, for example, approximately 1.5. Once the threshhold intensity value TH is calculated, the $\lambda_3$ intensity $I_3$ is compared with the threshhold intensity value. If the intensity $I_3$ is not greater than the threshhold intensity value, then the intensities $I_1$, $I_2$, and $I_3$ are stored by the central processor 14 into the memory 58. In the embodiment of FIG. 1, each intensity $I_1$, $I_2$, and $I_3$ is stored into the memory 58 and may further be separately accumulated to each form a weighted moving average for the respective wavelengths with a period of approximately five seconds.

However, if the intensity $I_3$ is greater than the threshhold intensity value, then the central processor 14 sets each intensity $I_1$, $I_2$ and $I_3$ to zero and stores these zero values into memory as part of the aforementioned weighted moving averages. It is to be noted that because equation 8 referred to above from the referenced Shaw, et al., patent is based on ratios of reflected radiation intensitites, the accumulation of zero individual radiation intensity values $I_1$, $I_2$, and $I_3$ has no influence on the ultimately calculated blood oxygen saturation.

With continued reference to FIGS. 1 and 3, if the central processor 14 determines that the intensity $I_3$ is greater than the base line intensity value, the central processor 14 then determines whether the intensity $I_3$ has been greater than the base line intensity value for a predetermined time period which can be approximately five seconds, although other time lengths may be suitably selected. This may be accomplished, for example, by programming the central processor 14 to measure a time interval in a fashion which is well known to those skilled in the art. If the intensity $I_3$ has not been greater than the base line intensity value for the five second time period, then the central processor 14 determines a new base line intensity value according to $BL = (1 + K_2) \cdot BL$, where $K_2$ is a predetermined constant that can be, for example, approximately 0.004. The new base line intensity value is then used to calculate a new threshhold intensity value which is compared to the intensity $I_3$ as described above.

If, however, the intensity $I_3$ has been greater than the base line intensity value for the predetermined time period, then the base line intensity value is increased so that $BL = (1 + K_3) \cdot BL$, where $K_3$ is a predetermined constant that can have an exemplary value of approximately 0.120. Once the base line intensity value has been adjusted in this way, then the threshhold intensity value is again determined and the remaining steps are performed by the central processor 14 as described above.

Thus, it is apparent that the method of FIG. 3 as implemented by the apparatus 10 of FIG. 1 adjusts a base line intensity value which generally follows the low-level portions of the $\lambda_3$ intensity $I_3$. As seen in FIG. 2, the $\lambda_3$ intensity $I_3$ plotted as the curve 58 thus may be thought to generally ride along or in relatively close proximity to a base line intensity value represented by a curve 62. The base line intensity value is continually updated in order to maintain this relationship. If the $\lambda_3$ intensity 58 is not greater than the base line intensity value 62, the base line is gradually decreased. On the other hand, if the $\lambda_3$ intensity 58 is greater than the base line intensity value 62, then the base line intensity value is increased by an amount related to the length of time that the $\lambda_3$ intensity has exceeded the base line intensity value. More particularly, if the $\lambda_3$ intensity 58 has been greater than the base line intensity value for not longer than the predetermined time period, then the base lline intensity value is slightly increased for each $\lambda_3$ intensity comparison. However, if the $\lambda_3$ intensity $I_3$ has been greater than the base line intensity value for longer than the predetermined time period, then the base line intensity value is increased relatively quickly with respect to the previous base line intensity value to thereby quickly adjust the base line intensity value with respect to the $\lambda_3$ intensity.

Once the base line intensity value is adjusted in this way, then the threshhold intensity value represented by the dashed line 64 in FIG. 2 is determined with respect to the base line intensity value. If the $\lambda_3$ intensity 58 is greater than the threshhold intensity value 64, the $\lambda_1$, $\lambda_2$ and $\lambda_3$ intensities $I_1$, $I_2$ and $I_3$ are set to zero and are then stored into the memory 58 as part of a moving average accumulation. Conversely, if the $\lambda_3$ intensity is not greater than the threshhold intensity value, then the $\lambda_1$, $\lambda_2$ and $\lambda_3$ intensities read by the central processor 14 from the optical module interface 16 are then stored into the memory 58 as part of the moving average accumulation. In this way, the threshhold intensity value determines the level above which the $\lambda_3$ intensity $I_3$ in particular and the associated $\lambda_1$ and $\lambda_2$ intensities $I_1$ and $I_2$ are presumed to be invalid. The moving average values for the intensities $I_1$, $I_2$ and $I_3$ are then used to determine oxygen saturation as described above.

It is to be understood that the predetermined constants $K_1$–$K_4$ can be varied according to the particular system requirements. Moreover, the adjustments to the base line intensity value can be fixed rather than related to the constants $K_1$–$K_3$ which will be readily apparent to those skilled in the art. It will be further apparent that the base line intensity value BL can be written in terms of the threshhold intensity value TH and the threshhold intensity value TH can therefore be considered to be adjusted directly with respect to the intensity $I_3$.

Thus, the signal filter method of FIG. 3 and the apparatus 10 of FIG. 1 provide an improved oximeter apparatus less susceptible to the pulsatile reflected radiation intensities indicative of erroneous or unuseable data. The steps set forth in FIG. 3 can, of course, be implemented using well-known software techniques with the central processor 14.

Figure 4:
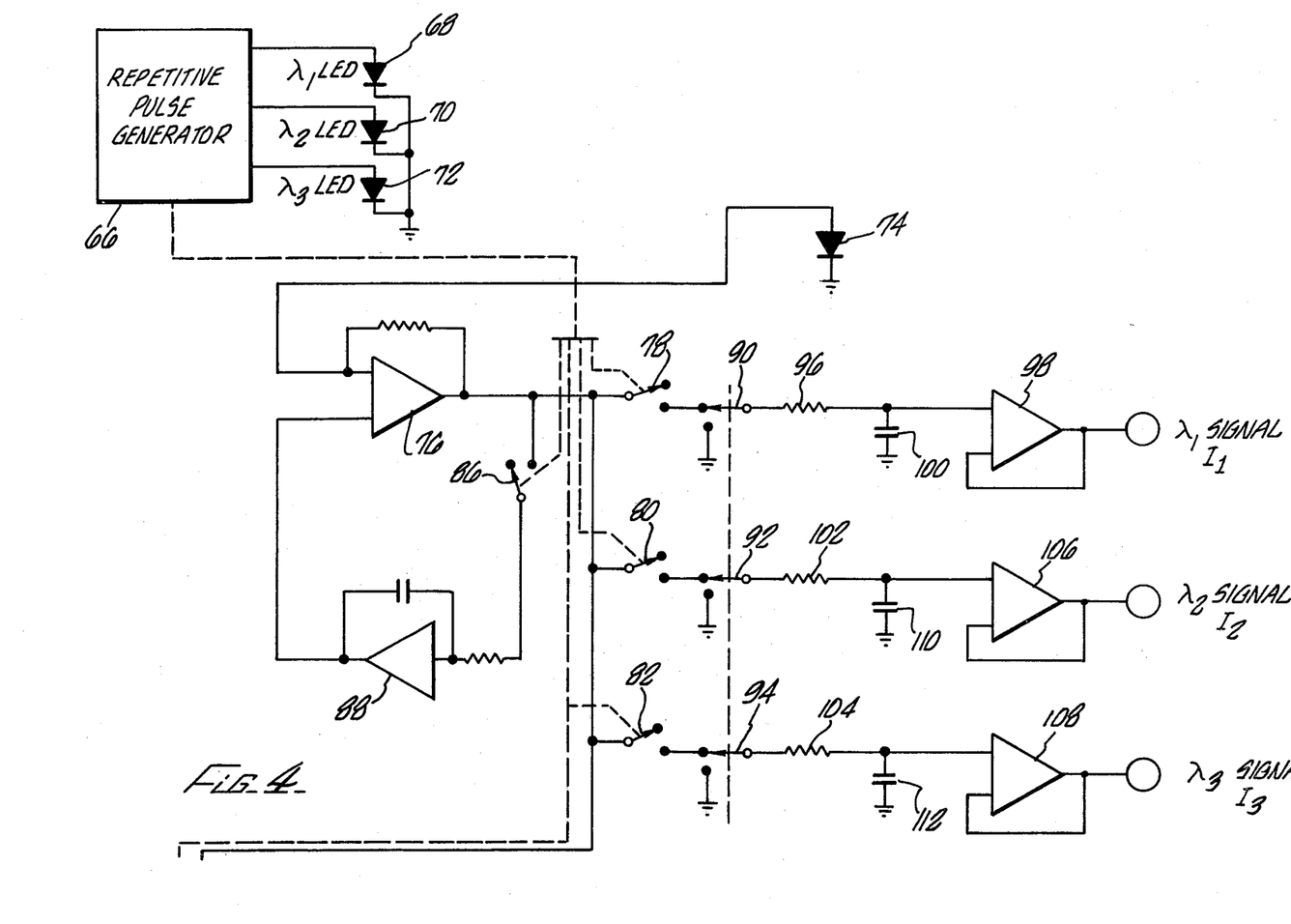
FIG. 4 is a portion of FIG. 1 of the Shaw, et al., patent referenced above modified for use with an alternative embodiment of the present invention.
Figure 5:
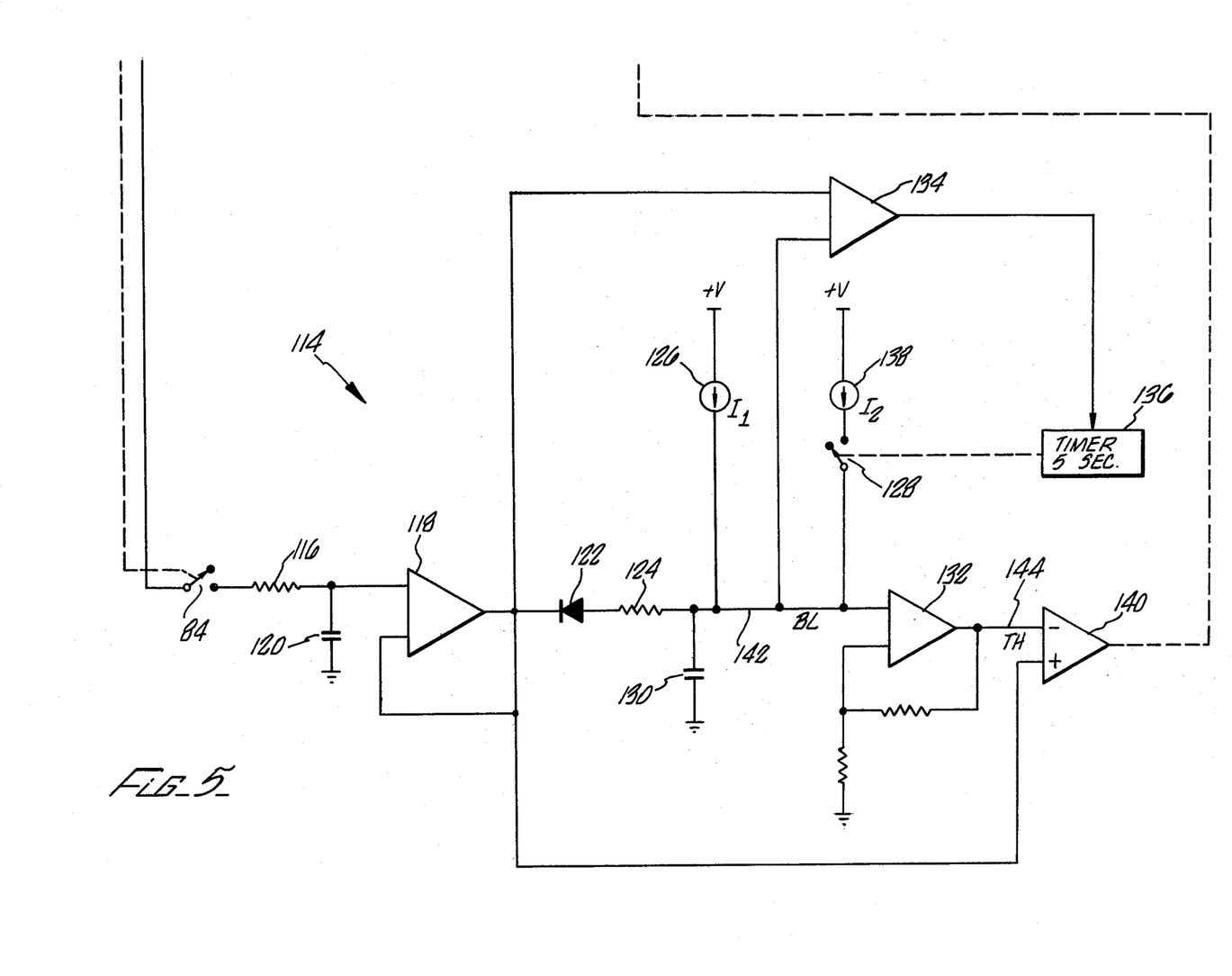
FIG. 5 is an alternative embodiment of the signal filter of the present invention adapted for use with the modified circuitry of FIG. 4.

With reference now to FIGS. 4 and 5, the apparatus disclosed in the referenced Shaw, et al., patent may be modified to incorporate the signal filter in accordance with the present invention.

As shown in FIG. 4, such an apparatus includes a repetitive pulse generator 66 which sequentially energizes a plurality of light-emitting diodes (LED's) 68, 70 and 72. The LEDs 68, 70 and 72 are coupled through a suitable optical combiner, optical integrator, and catheter as, for example, shown in FIG. 1, to provide to a detector 74 back-scattered and reflected radiation from the catheter tip. The LEDs 68, 70 and 72 emit radiation at three predetermined wavelengths $\lambda_1$, $\lambda_2$ and $\lambda_3$ as previously described above with reference to FIG. 1.

The detector 74 provides a signal representative of the radiation from the catheter tip to an amplifier 76, the output of which is connected to a plurality of normally open switches 78, 80, 82, 84 and 86 (FIGS. 4 and 5). The switches 78 and 80 are controlled by the generator 66 so as to be closed during the time that the LED's 68 and 70, respectively, emit radiation. Similarly, the switches 82 and 84 are controlled by the generator 66 so as to be closed during the portion of time that the LED 72 emits radiation. Lastly, the switch 86, as controlled by the generator 66, is closed when none of the LED's 68-72 is emitting, thus forming a closed loop servo system between the amplifier 76 and an amplifier 88 which establishes a bias voltage on the amplifier 76 that adjusts its output voltage to zero.

The switches 78-82 are in turn connected to normally closed switches 90-94 respectively. The swtich 90 is connected through a resistor 96 to an amplifier 98 and a capacitor 100. Similarly, the switches 92 and 94 are connected through resistors 102 and 104 to amplifiers 106 and 108 and to capacitors 110 and 112. The amplifiers 98, 106 and 108 provide $\lambda_1$, $\lambda_2$ and $\lambda_3$ radiation intensity output signals $I_1$, $I_2$ and $I_3$, respectively.

As shown with reference to FIG. 5, the switch 84 connects the signal from the amplifier 76 to signal filter circuitry designated generally 114. The switch 84 is connected through a resistor 116 to an amplifier 118 and a capacitor 120. The output of the amplifier 118 is connected to the anode of a diode 122, the cathode of which is connected through a resistor 124 via a line 142 to a first current source 126, a switch 128, a capacitor 130, an amplifier 132 and a comparator 134. The output of the amplifier 118 is also connected to a second input of the comparator 134. The output of the comparator 134 controls a timer 136 which in turn controls the switch 128. The switch 128 is also connected to a second current source 138. The output of the amplifier 132 is connected through a line 144 to the inverting input of a comparator 140, the non-inverting input of which is connected to the output of the amplifier 118. The output of the comparator controls the position of the switches 90, 92 and 94.

In operation, when the LED 72 emits radiation and the switches 82 and 84 are closed, the radiation from the catheter is detected by the detector 74. The detector 74 output is amplified by the amplifier 76 which applies a signal through the switch 84 to the amplifier 118. The current source 126 continuously provides current to the line 142 the signal on this line being proportional to a base line intensity value (BL), hereinafter referred to as a base line signal. The current source 126 increases the base line signal by a predetermined amount with respect to time, that is to say, at a predetermined rate. This base line signal is scaled or multiplied by the amplifier 132 to provide a threshhold signal (TH) on the line 144 to the comparator 140.

When the output of the amplifier 118 is less than the base line signal on the line 142, the capacitor 130 discharges through the resistor 124 and the diode 122 to thus decrease the base line signal on the line 142 and in turn proportionally decrease the threshhold signal on the line 144. If the output of the amplifier 118 is greater than the base line signal, however, then the current source 126 provides a first current to the line 142 to thereby increase the base line signal. Furthermore, if the output of the amplifier 118 is greater than the threshhold signal on the line 144, then the comparator 140 controls the switches 90-94 (FIG. 4) to connect the resistors 96, 102 and 104 to ground to thereby disable the further application of the signal from the amplifier 76 through the switches 78, 80 and 82. In this way, if the radiation intensity $I_3$ is greater than the threshhold signal on the line 144, indicating that erroneous radiation information is returning from the catheter, the signals proportional to the radiation intensities $I_1$, $I_2$, and $I_3$ are removed from the inputs to the amplifiers 98, 106 and 108.

If the output of the amplifier 118 remains greater than the base line signal for more than five seconds, the comparator 134 and the timer 136 control the switch 128 to connect the second current source 138 to the line 142. The second current source 138 provides a fixed current to the line 142 which relatively quickly increases the base line signal thereon. As with the current source 126, the current source 138 increases the base line signal by a predetermined amount with respect to time, which is to say, at a predetermined rate.

Thus it is seen that the signal filter circuitry 114, in accordance with the present invention, provides a base line signal which generally follows the low-level portions of the radiation intensity $I_3$. A threshhold signal is provided which is related to the base line signal, and if the radiation intensity $I_3$ is greater than this threshhold signal, then the signals corresponding to the radiation intensities $I_1$, $I_2$ and $I_3$ are not applied to the respective amplifiers 98, 106, and 108. It is to be further noted that the circuitry 114 provides an analog implementation of the signal filter method of FIG. 3.

Having thus described one embodiment of our invention in detail, it is to be understood that numerous equivalents and alterations which do not depart from the invention will be apparent to those skilled in the art, given the teachings herein. Thus, our invention is not to be limited to the above description but is to be of the full scope of the appended claims.

What is claimed is:

1. A method for filtering a signal including the steps of
   receiving the signal,
   generating a base line representation,
   varying the base line representation by a predetermined amount to adjust the base line representation toward the signal,
   determining a threshold representation related to the base line representation,
   comparing the signal with the threshold representation,
   transmitting the signal if the signal is less than the threshold representation, and
   transmitting a predetermined output if the signal is greater than the threshold representation.

2. A method as in claim 1 wherein said step of varying a base line representation is performed at a predetermined rate.

3. A method for filtering a signal including the steps of
receiving the signal,
generating a base line representation,
comparing the signal to the base line representation,
increasing the base line representation by a first amount when the signal is greater than the base line representation,
decreasing the base line representation by a second amount proportional to the difference between the base line representation and the signal when the signal is less than the base line representation,
generating a threshold representation as a function of the base line representation,
comparing the signal to the threshold representation,
transmitting the signal if the signal is less than the threshold representation, and
transmitting a predetermined output if the signal is greater than the threshold representation.

4. An apparatus for filtering a signal comprising
means for receiving the signal,
base line means responsive to the received signal for generating a base line representation, said base line means including a circuit means for varying the base line representation by a predetermined amount to adjust the base line representation toward the signal,
threshold means responsive to the base line representation for generating a threshold representation as a function of the base line representation,
comparator means responsive to the received signal and to the threshold representation for comparing the signal to the threshold representation and for transmitting the signal if the signal is less than the threshold representation.

5. An apparatus as in claim 4 wherein the base line means further includes means for increasing the base line representation by a first predetermined amount when the signal is greater than the base line representation and for decreasing the base line representation by a second predetermined amount when the signal is less than the base line representation.

6. An apparatus as in claim 5 wherein said first predetermined amount is varied in accordance with the length of time that the signal is greater than the base line representation.

7. An apparatus for filtering a signal including
means for receiving the signal,
first means responsive to the received signal for generating a base line representation and for comparing the signal to the base line representation,
second means responsive to the first means for increasing the base line representation by a first predetermined amount when the signal exceeds the base line representation for less than a predetermined time period and for increasing the base line representation by a second predetermined amount when the signal exceeds the base line representation for longer than the predetermined time period,
third means responsive to the first means for decreasing the base line representation by a predetermined amount proportional to the difference between the base line representation and the signal when the signal is less than the base line representation,
fourth means responsive to the base line representation for determining a threshold representation as a function of the base line representation,
fifth means responsive to the received signal and to the threshold representation for comparing the signal to the threshold representation,
output means responsive to the received signal for providing an output of the signal when the signal is less than the threshold representation and for providing an output of a second signal when the first signal is greater than the threshold representation.

8. In a method of determining oxygen saturation of blood comprising the steps of
producing electro-magnetic radiation at a plurality of different wavebands,
coupling the electro-magnetic radiation of the wavebands to blood under test,
detecting radiation at each of the wavebands received back from the blood under test for producing corresponding electrical signals representative of the intensity of the radiation received back from the blood under test at the respective waveband, and
providing an output manifestation of oxygen saturation as a function of the electrical signals;
a method for filtering the electrical signals including the steps of
selecting one of the electrical signals,
generating a threshold representation,
adjusting the threshold representation by increasing the threshold representation when the selected electrical signal is greater than a predetermined fraction of the threshold representation and decreasing the threshold representation when the selected electrical signal is less than the predetermined fraction of the threshold representation,
comparing the selected electrical signal with the adjusted threshold representation, and enabling the step of providing an output manifestation of oxygen saturation when the selected electrical signal is greater than the threshold representation.

9. A method as set forth in claim 8, wherein the step of generating a threshold representation includes the further step of generating a base line representation proportional to the threshold representation.

10. A method as in claim 9 wherein the step of generating a base line representation includes the further step of generating a base line representation having a value equal to the predetermined fraction of the threshold voltage and the step of adjusting the threshold representation includes the further step of increasing the base line representation by a first amount when the selected electrical signal is greater than the base line representation and decreasing the base line representation by a second amount when the selected electrical signal is less than the base line representation.

11. A method as in claim 10 wherein the first amount is varied in accordance with the length of time that the selected electrical signal is greater than the base line representation.

12. In a method for determining oxygen saturation of blood comprising the steps of
producing electro-magnetic radiation at a plurality of different wavebands,
coupling the radiation at the different wavebands to blood under test,
detecting radiation at each of the wavebands received back from the blood under test for producing a corresponding electrical signal representative of the intensity of the radiation received from the blood under test at each respective waveband, selecting one of the electrical signals, generating a base line representation, varying the value of the base line representation by a predetermined amount to adjust the base line representation toward the selected electrical signal, generating a threshold representation as a function of the base line representation, comparing the selected electrical signal with the threshold representation, generating a first series of outputs having values respectively representing the electrical signals if the selected electrical signal is less than the threshold representation, generating a second series of outputs having predetermined values if the selected electrical signal is greater than the threshold representation, summing the first and second series of outputs to provide summed electrical signals for the respective wavebands, and providing an output manifestation of oxygen saturation as a function of the summed electrical signals.

13. A method of determining oxygen saturation of blood comprising the steps of producing electro-magnetic radiation at a plurality of different wavebands, coupling the radiation at the different wavebands to blood under test, detecting radiation at each of the wavebands received back from the blood under test for producing a corresponding electrical signal representative of the intensity of the radiation received back from the blood under test at the respective waveband, selecting one of the electrical signals, generating a base line signal, comparing the selected electrical signal to the base line signal, increasing the base line signal by an amount proportional to the base line signal when the selected electrical signal is greater than the base line signal, decreasing the base line signal by an amount proportional to the difference between the base line signal and the selected electrical signal when the selected electrical signal is less than the base line signal, generating a threshold signal related to the base line signal by a predetermined ratio, comparing the selected electrical signal with the threshold signal, generating a first series of outputs having values respectively representing the electrical signals when the selected electrical signal is less than the threshold signal, generating a second series of outputs having predetermined values when the selected electrical signal is greater than the threshold signal, summing the first and second series of outputs to provide a summed electrical signal for each respective waveband, and providing an output manifestation of oxygen saturation as a function of the summed electrical signals.

14. A method as in claim 13 wherein the electrical signals, the base line signal and the threshold signal are digital signals.

15. A method as in claim 13 wherein the electrical signals, the base line signal and the threshold signal are analog signals.

16. A method as set forth in claims 12 or 13, wherein said step of coupling the radiation at the different wavebands to blood under test includes the further steps of transmitting the radiation at each different waveband to the blood and test along a single transmitting optical fiber and receiving radiation reflected back from the blood under test at each different waveband along a single receiving optical fiber.

17. In an apparatus for determining oxygen saturation of blood comprising source means for producing electro-magnetic radiation at a plurality of wavelengths, means adapted to be coupled to the source means for supplying the radiation therefrom to blood under test with incident intensities at the respective wavelengths, detector means adapted to receive radiation back from the blood under test for producing signals representative of the intensities of the radiation received thereby at the respective wavelengths, and determining means responsive to the detector means for receiving the signals therefrom and for determining an output manifestation of oxygen saturation as a function of the signals;

an apparatus for filtering the signals including first means responsive to a selected one of said signals for generating a threshold representation and for adjusting the value of the threshold representation by increasing the threshold representation a first predetermined amount when the selected signal is greater than a predetermined fraction of the value of the threshold representation and for decreasing the threshold representation a second predetermined amount when the selected signal is less than the predetermined fraction of the value of the threshold representation, second means responsive to the selected signal and responsive to the adjusted threshold representation for comparing the selected signal with the adjusted threshold representation, and switch means being responsive to the second means for supplying the signals from the detector means to the determining means when the selected signal is less than the threshold representation.

18. In an apparatus for determining oxygen saturation of blood comprising source means for producing electro-magnetic radiation at a plurality of wavelengths, means adapted to be coupled to the source means for supplying the radiation therefrom to blood under test with incident intensities at the respective wavelengths, detector means adapted to receive radiation back from the blood under test for producing signals representative of the intensities of the radiation received thereby at the respective wavelengths, and determining means responsive to the detector means for determining an output manifestation of oxygen saturation according to the relationship between the signals;

an apparatus for filtering the signals including first means responsive to at least a selected one of said signals for generating a base line representation and for varying the value of the base line representation to adjust the base line representation toward the selected signal, second means responsive to the base line representation for generating a threshold representation proportional to the base line representation, third means responsive to the selected signal and to the threshold representation for comparing the selected signal to the threshold representation, and switch means responsive to the third means for supplying the signals from the detector means to the determining means when the selected signal is less than the threshold representation.

19. An apparatus as in claim 18 wherein the first means further includes means for increasing the base line representation by a first amount when the selected signal is greater than the base line representation and for decreasing the base line representation by a second amount when the selected signal is less than the base line representation.

20. An apparatus as in claim 19 wherein the first amount is varied in accordance with the length of time that the selected signal is greater than the base line representation.

21. An apparatus for determining oxygen saturation of blood comprising source means for producing electro-magnetic radiation at a plurality of wavelengths, means adapted to be coupled to the source means for supplying the radiation therefrom to blood under test with incident intensities at the respective wavelengths, detector means adapted to receive radiation back from the blood under test for producing signals representative of the intensities of the radiation received thereby at the respective wavelengths, first means responsive to a selected one of said signals for generating a base line representation and for comparing the selected signal to the base line representation, second means responsive to the first means for increasing the base line representation by a first amount when the selected signal exceeds the base line representation for less than a predetermined time period and for increasing the base line representation by a second amount when the selected signal exceeds the base line representation for more than the predetermined time period, third means responsive to the first means for decreasing the base line representation by an amount proportional to the difference between the base line representation and the selected signal when the signal is less than the base line representation, fourth means responsive to the base line representation for determining a threshold representation related to the base line representation by a predetermined ratio, fifth means responsive to the selected signal and to the threshold representation for comparing the selected signal to the threshold representation, output means responsive to the selected signal for providing a first series of outputs having values representing the signals when the selected signal is less than the threshold representation and for providing a second series of outputs having predetermined values when the selected signal is greater than the threshold representation, summing means responsive to the first and second series of outputs for summing the first and second series of outputs to provide a summed signal for each respective waveband, and determining means responsive to the summed signals for determining an output manifestation of oxygen saturation as a function of the summed signals.

22. An apparatus as in claim 21 wherein the base line representation and the threshold representation are digital signals.

23. An apparatus as in claim 21 wherein the base line representation and the threshold representation are analog signals.

24. An apparatus as in claim 21 wherein the second means and the third means adjust the base line representation at predetermined rates.

25. An apparatus as set forth in claims 17, 18 or 21, wherein said means adapted to be coupled to the source means includes a catheter having a single transmitting optical fiber and a single receiving optical fiber.

26. A method for filtering a data signal, said method including the steps of:

generating a threshold signal;

receiving the data signal;

adjusting said threshold signal by decreasing the value of said threshold signal a first amount when the value of the data signal is less than a predetermined fraction of the value of said threshold signal and increasing the value of said threshold signal a second amount when the value of the data signal is greater than said predetermined fraction of the value of said threshold signal;

comparing the data signal with said threshold signal; and transmitting the data signal if the value of the data signal is less than the value of said threshold signal.

27. A method as set forth in claim 26, wherein said step of adjusting said threshold signal further includes the step of generating a base line signal having a value equal to said predetermined fraction of the value of said threshold signal, said step of adjusting said threshold signal further including the step of decreasing the value of said threshold signal by said first amount when the value of the data signal is less than the value of said base line signal and increasing the value of said threshold signal by said second amount when the value of the data signal is greater than the value of said base line signal.

28. A method as set forth in claim 27, wherein said step of generating said threshold signal includes the further step of amplifying said base line signal.

29. A method as set forth in claim 27, wherein said first amount is equal to $K_1(BL-I_3)$, where $K_1$ is a predetermined fractional constant, BL is the value of the base line signal and I is the value of the data signal.

30. A method as set forth in claim 29, wherein said step of adjusting said threshold signal includes the further step of determining whether the value of the data signal exceeds the value of said base line signal for more than a predetermined length of time.

31. A method as set forth in claim 30, wherein said second amount is varied in accordance with said determination of whether the value of the data signal exceeds the value of said base line signal for more than said predetermined length of time.

32. A method as set forth in claim 31, wherein said second amount is determined in accordance with one of two equations depending upon whether the value of the data signal exceeds the value of said base line signal for more than said predetermined length of time.

33. A method as set forth in claim 32, wherein said second amount is determined in accordance with the equation $BL=(1+K_2)BL$, where BL is the value of the base line signal and $K_2$ is a predetermined fractional constant, when the value of the data signal has not exceeded the value of said base line signal for more than said predetermined length of time.

34. A method as set forth in claim 32, wherein said second amount is computed in accordance with the equation $BL=(1+K_3)BL$, where BL is the value of said base line signal and $K_3$ is a third predetermined constant, when the value of the data signal has exceeded the value of said base line signal for more than said predetermined length of time.

35. A method for filtering a data signal which varies in pulsatile fashion, said method comprising the steps of:
generating a base line signal having a base line value;
receiving the data signal;
varying said base line value of said base line signal such that said base line signal tracks the data signal;
generating a threshold signal having a threshold value proportional to said base line value;
comparing the data signal with said threshold signal; and
transmitting only those portions of the data signal having values less than said threshold value.

36. A method for determining oxygen saturation levels in blood undergoing analysis, said method comprising the steps of: P1 generating electromagnetic radiation at a plurality of different wavelengths;
transmitting said electromagnetic radiation at each of said plurality of different wavelengths to the blood undergoing analysis;
receiving electromagnetic radiation back from the blood undergoing analysis at each of said plurality of different wavelengths in response to the reflection of said electromagnetic radiation transmitted to the blood at each of said plurality of different wavelengths;
detecting the electromagnetic radiation so received at each of said plurality of different wavelengths;
generating a plurality of data signals, each of said plurality of data signals having a value which varies in proportion to the intensity of said electromagnetic radiation so received at one of said plurality of different wavelengths;
selecting one of said data signals;
generating a threshold signal having a threshold value which varies in response to variations in the value of said one of said data signals so selected;
comparing said one of said data signals so selected with said threshold signal; and
generating an output signal as a function of said plurality of data signals when the value of said one of said plurality of data signals so selected is less than said threshold value, said output signal having a value representing the oxygen saturation level of the blood undergoing analysis.

37. A method as set forth in claim 36, wherein said step of transmitting electromagnetic radiation to the blood undergoing analysis includes the further step of transmitting said electromagnetic radiation along a single optical transmitting fiber at each of said plurality of different wavelengths and said step of receiving electromagnetic radiation back from the blood undergoing analysis includes the further step of receiving said electromagnetic radiation along a single optical receiving fiber at each of said plurality of different wavelengths.

38. An apparatus for determining oxygen saturation levels in blood undergoing analysis, said apparatus comprising:
source means for generating electromagnetic radiation at a plurality of different wavelengths;
fiberoptic means coupled to said source means for transmitting said electromagnetic radiation at each of said plurality of different wavelengths to the blood undergoing analysis and for receiving electromagnetic radiation reflected back from the blood at each of said plurality of different wavelengths in response to said electromagnetic radiation so transmitted;
detector means coupled to said fiberoptic means for generating a plurality of signals respectively having values which vary in proportion to the intensities of said electromagnetic radiation received by said fiber optic means at each of said plurality of different wavelengths;
a filter means connected to said detector means for receiving a selected one of said plurality of signals, said filter means including a circuit means for generating a threshold signal having a value which varies in response to the variation in value of said selected one of said signals and for comparing said threshold signal with said selected one of said plurality of data signals in order to generate a filter output signal when the value of said selected one of said plurality of data signals is less than the value of said threshold signal; and
computing means connected to said filter means for generating an oxygen saturation output signal as a function of said plurality of data signals in response to the generation of said filter output signal by said filter means.

39. An apparatus as set forth in claim 38, wherein said fiberoptic means includes a first fiberoptic guide means for transmitting said electromagnetic radiation at each of said plurality of different wavelengths to the blood undergoing analysis and a second fiberoptic guide means for receiving said electromagnetic radiation reflected back from the blood at each of said plurality of different wavelengths.

40. An apparatus as set forth in claim 39, wherein said first fiberoptic guide means is a single optical transmitting fiber and said second fiberoptic guide means is a single optical receiving fiber.

* * * * *